United States Patent
Dyllick-Brenzinger et al.

Patent Number: 5,487,770
Date of Patent: Jan. 30, 1996

[54] DETECTION OF MARKED MINERAL OILS AND NOVEL AZO DYES

[75] Inventors: Rainer Dyllick-Brenzinger, Weinheim; Friedrich-Wilhelm Raulfs, Ludwigshafen; Ulrike Schlösser, Ludwigshafen; Karin H. Beck, Ludwigshafen; Gerhard Scholz, Ludwigshafen, all of Germany

[73] Assignee: BASF Aktiengesellschaft, Ludwigshafen, Germany

[21] Appl. No.: 321,629

[22] Filed: Oct. 12, 1994

[30] Foreign Application Priority Data

Oct. 12, 1993 [DE] Germany .................. 43 34 678.2

[51] Int. Cl.⁶ .................................... C10L 1/22
[52] U.S. Cl. ................ 44/328; 534/558; 534/573
[58] Field of Search ............................. 44/328

[56] References Cited

U.S. PATENT DOCUMENTS

| | | | |
|---|---|---|---|
| 2,925,333 | 2/1960 | Thompson | 44/328 |
| 3,690,809 | 9/1972 | Orelup | 44/328 |
| 3,704,106 | 11/1972 | Orelup | 44/328 |
| 3,764,273 | 10/1973 | Turner et al. | 23/230 R |
| 4,473,376 | 9/1984 | Hansen et al. | 44/328 |
| 4,479,899 | 10/1984 | Hamprecht | 44/328 |
| 4,904,765 | 2/1990 | Derber et al. | 44/328 |
| 5,156,653 | 10/1992 | Friswell et al. | 44/328 |
| 5,252,106 | 10/1993 | Hallisy | 44/328 |

*Primary Examiner*—Ellen M. McAvoy

*Attorney, Agent, or Firm*—Oblon, Spivak, McClelland, Maier & Neustadt

[57] ABSTRACT

Method for detecting marked mineral oils by treating the marked mineral oil with an extractant comprising water, a solvent and a base comprises using as marker an azo dye of the formula

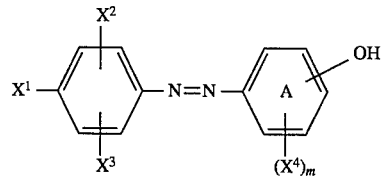

where ring A may be benzofused, m is from 1 to 4, $X^1$ is hydrogen, $C_1$–$C_4$-alkyl, cyano or nitro, $X^2$ is hydrogen, $C_1$–$C_4$-alkyl, cyano, nitro, $C_1$–$C_4$-alkoxy or $C_1$–$C_{16}$-alkoxycarbonyl, $X^3$ is hydrogen, $C_1$–$C_4$-alkyl, cyano or $C_1$–$C_{16}$-alkoxycarbonyl, and $X^4$ is hydrogen, hydroxyl, substituted or unsubstituted $C_1$–$C_8$-alkyl, $C_1$–$C_4$-alkoxy, amino, $C_1$–$C_4$-dialkylamino or substituted or unsubstituted $C_1$–$C_{16}$-monoalkylamino, as solvent a partially or completely water-miscible organic solvent, and as base an alkali or alkaline earth metal hydroxide, an alkali metal carbonate or a quaternary ammonium hydroxide, the use of azo dyes as markers for mineral oils, and novel azo dyes.

10 Claims, No Drawings

DETECTION OF MARKED MINERAL OILS AND NOVEL AZO DYES

The present invention relates to a novel method for detecting azo dye marked mineral oils, the use of monoazo or disazo dyes as markers for mineral oils, and novel azo dyes.

U.S. Pat. No. 5,156,653 discloses the use of phenylazophenols for marking mineral oils. The markers are detected there by shaking the marked mineral oil with a mixture of water, diethylene glycol and methoxyethoxypropylamine to form a mineral oil phase and an aqueous phase containing the azo dye. However, it has been found that the method of detection described there is not satisfactory. It does not have universal utility and frequently produces only an extremely weak coloring of the aqueous phase, since some of the dye used remains in the oil phase.

U.S. Pat. No. 3,764,273 describes the extraction of quinizarin derivatives and of specific azo dyes, inter alia with aqueous alkali and dimethyl sulfoxide.

Finally, U.S. Pat. No. 5,252,106 discloses the use of 4-(4'-phenylazophenylazo)phenols for marking mineral oils.

It is an object of the present invention to provide a novel method for detecting azo dye marked mineral oils which is simple to carry out and by means of which the markers, even in low concentrations, can be visibilized by strong color reaction.

We have found that this object is achieved by a method for detecting azo dye marked mineral oils by treating the marked mineral oil with an extractant comprising water, a solvent and a base, the azo dye transferring from the mineral oil into the aqueous phase, which comprises using as marker an azo dye of the formula I

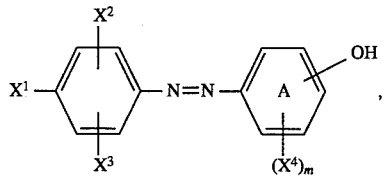

where
ring A may be benzofused,
m is from 1 to 4,
$X^1$ is hydrogen, $C_1$–$C_4$-alkyl, cyano or nitro,
$X^2$ is hydrogen, $C_1$–$C_4$-alkyl, cyano, nitro, $C_1$–$C_4$-alkoxy or $C_1$–$C_{16}$-alkoxycarbonyl,
$X^3$ is hydrogen, $C_1$–$C_4$-alkyl, cyano or $C_1$–$C_{16}$-alkoxycarbonyl, and
$X^4$ is hydrogen, hydroxyl, $C_1$–$C_8$-alkyl, which may be phenyl-substituted, $C_1$–$C_4$-alkoxy, amino, $C_1$–$C_4$-dialkylamino or $C_1$–$C_{16}$-monoalkylamino whose alkyl chain may be interrupted by from 1 to 3 oxygen atoms in the ether function,
as solvent a partially or completely water-miscible organic solvent, and as base an alkali or alkaline earth metal hydroxide, an alkali metal carbonate or an ammonium compound of the formula

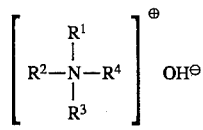

where $R^1$, $R^2$, $R^3$ and $R^4$ are each independently of the others $C_1$–$C_{16}$-alkyl or benzyl.

Any alkyl appearing in the abovementioned formulae may be straight-chain or branched.

Unless otherwise stated, substituents in substituted phenyl or naphthyl appearing in the abovementioned formula need not all be the same.

$X^1$, $X^2$, $X^3$, $X^4$, $R^1$, $R^2$, $R^3$ and $R^4$ are each for example methyl, ethyl, propyl, isopropyl, butyl, isobutyl or sec-butyl.

$X^4$, $R^1$, $R^2$, $R^3$ and $R^4$ may each also be for example pentyl, isopentyl, neopentyl, tert-pentyl, hexyl, 2-methylpentyl, heptyl, octyl, 2-ethylhexyl or isooctyl.

$R^1$, $R^2$, $R^3$ and $R^4$ may each also be for example nonyl, isononyl, decyl, isodecyl, undecyl, dodecyl, tridecyl, 3,5,5,7-tetramethylnonyl, isotridecyl, tetradecyl, pentadecyl or hexadecyl (the above designations isooctyl, isononyl, isodecyl and isotridecyl are trivial names derived from the oxo process alcohols - cf. Ullmanns Encyclopädie der technischen Chemie, 4th edition, Volume 7, pages 215 to 217, and Volume 11, pages 435 and 436).

$X^4$ may also be for example dimethylamino, diethylamino, dipropylamino, diisopropylamino, dibutylamino, methylamino, ethylamino, propylamino, isopropylamino, butylamino, isobutylamino, sec-butylamino, pentylamino, isopentylamino, neopentylamino, tert-pentylamino, hexylamino, 2-methylpentylamino, heptylamino, octylamino, 2-ethylhexylamino, isooctylamino, nonylamino, isononylamino, decylamino, isodecylamino, undecylamino, dodecylamino, tridecylamino, 3,5,5,7-tetramethylnonylamino, isotridecylamino, tetradecylamino, pentadecylamino, hexadecylamino, 2-methoxyethylamino, 2-ethoxyethylamino, 2-methoxypropylamino, 3,6-dioxaheptylamino, 3,6-dioxaoctylamino, 3,6,9-trioxadecylamino, 3,6,9-trioxaundecylamino, benzyl or 1- or 2-phenylethyl.

$X^2$ and $X^4$ may each also be for example methoxy, ethoxy, propoxy, isopropoxy, butoxy, isobutoxy or sec-butoxy.

$X^2$ and $X^3$ may each also be for example methoxycarbonyl, ethoxycarbonyl, propoxycarbonyl, isopropoxycarbonyl, butoxycarbonyl, isobutoxycarbonyl, sec-butoxycarbonyl, pentyloxycarbonyl, isopentyloxycarbonyl, neopentyloxycarbonyl, tert-pentyloxycarbonyl, hexyloxycarbonyl 2-methylpentyloxycarbonyl, heptyloxycarbonyl, octyloxycarbonyl, 2-ethylhexyloxycarbonyl, isooctyloxycarbonyl, nonyloxycarbonyl, isononyloxycarbonyl, decyloxycarbonyl, isodecyloxycarbonyl, undecyloxycarbonyl, dodecyloxycarbonyl, tridecyloxycarbonyl, isotridecyloxycarbonyl, tetradecyloxycarbonyl, pentadecyloxycarbonyl or hexadecyloxycarbonyl.

Attention is drawn in particular to a method of detection using azo dyes of the formula I where
$X^1$ is hydrogen or $C_1$–$C_4$-alkyl,
$X^2$ is hydrogen, $C_1$–$C_4$-alkyl, $C_1$–$C_4$-alkoxy or $C_1$–$C_{16}$-alkoxycarbonyl,
$X^3$ is hydrogen, $C_1$–$C_4$-alkyl, or $C_1$–$C_{16}$-alkoxycarbonyl, and
m, Y and $X^4$ are each as defined above.

Particular preference is given to using in the method of the invention azo dyes of the formula Ia

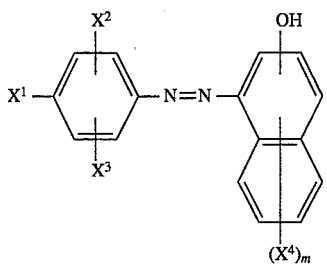

where
m is from 1 to 4, $X^1$ is hydrogen, cyano or nitro, $X^2$ is hydrogen, $C_1$–$C_4$-alkyl, $C_1$–$C_4$-alkoxy or $C_1$–$C_{13}$-alkoxycarbonyl, $X^3$ is hydrogen or $C_1$–$C_4$-alkyl, and $X^4$ is hydrogen or $C_1$–$C_4$-alkyl, which may be phenyl-substituted.

Particular preference is further given to using in the method of the invention azo dyes of the formula Ib

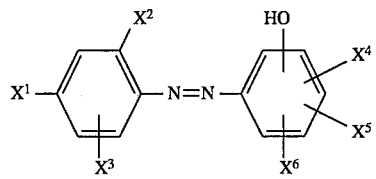

where $X^1$ is hydrogen, $X^2$ is hydrogen, $X^3$ is hydrogen or $C_1$–$C_4$-alkyl, $X^4$ is hydrogen, $C_1$–$C_4$-alkyl, $C_1$–$C_4$-dialkylamino or $C_1$–$C_{16}$-monoalkylamino, $X^5$ is hydrogen or $C_1$–$C_4$-alkyl, and $X^6$ is hydrogen, $C_1$–$C_4$-alkyl or $C_1$–$C_4$-alkoxy, with the proviso that a) at least one of the three radicals $X^1$, $X^2$ and $X^3$ is different from hydrogen, b) $X^2$ may also be cyano when $X^4$ is $C_1$–$C_4$-dialkylamino, c) $X^2$ may also be $C_1$–$C_4$-alkoxycarbonyl when all the radicals $X^4$, $X^5$ and $X^6$ are different from hydrogen, and d) one of the radicals $X^1$, $X^2$ or $X^3$ may also be nitro when $X^4$ is $C_1$–$C_{16}$-monoalkylamino and $X^6$ is $C_1$–$C_4$-alkyl.

Very particular preference is given to using in the method of the invention azo dyes of the formula Ia where $X^4$ is hydrogen or 1-phenylethyl.

Very particular preference is further given to using in the method of the invention azo dyes of the formula Ia where $X^1$ is hydrogen, $X^2$ is methyl or $C_1$–$C_{13}$-alkoxycarbonyl, and $X^3$ is hydrogen or methyl.

Suitable alkali or alkaline earth metal hydroxides or alkali metal carbonates for use in the method of the invention include for example lithium hydroxide, sodium hydroxide, potassium hydroxide, magnesium hydroxide, calcium hydroxide, lithium carbonate, sodium carbonate and potassium carbonate.

Suitable ammonium compounds include for example tetramethylammonium hydroxide, tetraethylammonium hydroxide, tetrapropylammonium hydroxide, tetrabutylammonium hydroxide, benzyltrimethylammonium hydroxide, benzyltriethylammonium hydroxide and benzyltributylammonium hydroxide.

The use of alkali or alkaline earth metal hydroxides as base is preferred with particular attention being drawn to alkali metal hydroxides.

Particular preference is given to the use of lithium hydroxide, sodium hydroxide or potassium hydroxide as base, sodium hydroxide being of particular importance.

Since the extractant includes water, the alkali or alkaline earth metal hydroxides, alkali metal carbonates or ammonium compounds are preferably used directly in the form of an aqueous solution, this aqueous solution generally having an alkali or alkaline earth metal hydroxide, alkali metal carbonate or ammonium compound content from 0.1 to 10% by weight, preferably from 1 to 10% by weight, each percentage being based on the weight of the aqueous solution.

Suitable solvents are partially or completely water-miscible organic solvents. This includes for example amides, especially carboxamides, such as formamide, N-methylformamide, N,N-dimethylformamide, N,N-diethylformamide, N,N-dimethylacetamide, pyrrolidin-2-one, 1-methylpyrrolidin-2-one (NMP), 1,3-dimethylhexahydropyrimid-2-one or hexamethylphosphoramide, N,N,N',N'-tetramethylguanidine, acetonitrile, nitromethane, amines, such as 2-aminoethanol, 1,10-diamino-4,7-dioxadecane, 1,13-diamino-4,7,10-trioxatridecane, 2- or 3-methoxypropylamine, 1,8-bis(dimethylamino)naphthalene or an amine of the formula $H_2N$—$CH(CH_3)CH_2[$—$OCH(CH_3)CH_2]_{2,6}$—$OCH_2CH$—($CH_3$)—$NH_2$, 1-methylpyrazole, dimethyl sulfoxide (DMSO) or sulfolane.

Preferred solvents are 1-methylpyrazole, pyrrolidin-2-one, 1-methylpyrrolidin-2-one, dimethyl sulfoxide and sulfolane.

In some cases it can also be of advantage for the extractant to include further admixtures, for example 4-nonylphenol, or for the mineral oil to have 4-nonylphenol added to it prior to the extraction.

Based on the weight of the extractant, the proportion of solvent typically ranges from 50 to 99% by weight, preferably from 90 to 99% by weight.

To mark mineral oil, the azo dyes of the formula I are used either without a solvent or in the form of solutions. Suitable solvents include preferably aromatic hydrocarbons, such as toluene, xylene, dodecylbenzene, diisopropylnaphthalene or a mixture of higher aromatics commercially available from Shell as Shellsol® AB. The solubility may be improved in a conventional manner by using further, co-solvents, for example alcohols, such as methanol, ethanol, propanol, isopropanol, butanol, isobutanol, pentanol, hexanol, heptanol, octanol, 2-ethylhexanol or cyclohexanol, glycols, such as butylethylene glycol or methylpropylene glycol, amines, such as triethylamine, diisooctylamine, dicyclohexylamine, aniline, N-methylaniline, N,N-dimethylaniline, toluidine or xylidine, alkanolamines, such as 3-(2-methoxyethoxy)propylamine, o-cresol, m-cresol, p-cresol, ketones, such as diethyl ketone or cyclohexanone, lactams, such as γ-butyrolactam, carbonates, such as ethylene carbonate or propylene carbonate, phenols, such as t-butylphenol or nonylphenol, esters, such as methyl phthalate, ethyl phthalate, 2-ethylhexyl phthalate, ethyl acetate, butyl acetate or cyclohexyl acetate, amides, such as N,N-dimethylformamide, N,N-diethylacetamide or N-methylpyrrolidin-2-one, or mixtures thereof. To avoid the resulting solution from becoming too viscous, it is generally advisable to use a concentration of azo dye I from 1 to 50% by weight, preferably from 10 to 50% by weight, each percentage being based on the solution.

In the course of the treatment of the marked mineral oil with the extractant, for example by shaking, the azo dye of the formula I transfers into the aqueous phase, which takes on a distinctly visible color in the process.

The method of the invention provides a very simple means of detecting mineral oils marked with azo dyes of the formula I. A further advantage of the method of the invention is that it permits the extraction of dyes which have only little acidity.

The present invention further provides for the use of azo dyes of the abovementioned formulae Ia and Ib for marking mineral oils.

Preference for marking mineral oils is given to the use of azo dyes of the formula Ia where $X^4$ is hydrogen or 1-phenylethyl.

Preference for marking mineral oils is further given to the use of azo dyes of the formula Ia where $X^1$ is hydrogen, $X^2$ is methyl or $C_1$–$C_{13}$-alkoxycarbonyl, and $X^3$ is hydrogen or methyl.

Particular preference for marking mineral oils is further given to the use of azo dyes of the formula Ic

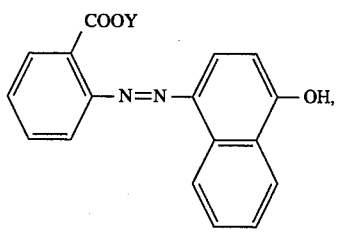

where Y is $C_7$–$C_{11}$-alkyl.

Mineral oils for the purposes of the present invention include for example motor fuels, such as gasoline, kerosine or diesel fuel, or oils, such as fuel oil or engine oil.

The azo dyes of the formula Ia or Ib are especially suitable for marking mineral oils where a form of identification is required, for example for tax reasons. To keep the costs for this to a minimum, it is desirable to keep the amount of marker used to a minimum.

Marking for the purposes of the present invention is the addition of the azo dyes of the formula Ia or Ib to mineral oils in such a concentration that, to the human eye, the mineral oils have barely any or no visible color, although the dyes of the formulae Ia and Ib are readily and distinctly visibly detectable by the methods of detection more particularly described herein.

To mark mineral oil, the azo dyes of the formula Ia or Ib, as mentioned above, are used either without a solvent or in the form of solutions.

The azo dyes of the formula Ia or Ib to be used according to the invention have the advantage of being suitable, depending on their concentration, of conferring a clearly visible color on mineral oils and/or for use as marker substances.

The azo dyes of the formula Ia or Ib to be used according to the invention permit very simple detection of marked mineral oils, even if the marker substances are present only in a concentration of about 10 ppm or less.

The azo dyes of the formula Ia have the application advantage of very good solubility and also excellent dilutability. Moreover, in the detection reaction, they give distinctly more bathochromic hues than the dyes known from U.S. Pat. No. 5,156,653.

It is a further object of the present invention to provide novel azo dyes which shall be advantageous for use as marker substances for mineral oils.

We have found that this object is achieved by the azo dyes of the formula II

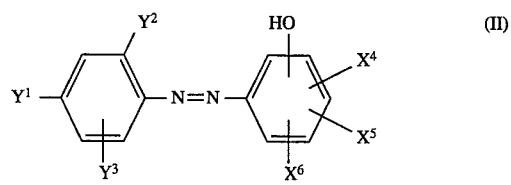

where $Y^1$ is hydrogen, or $C_1$–$C_4$-alkyl-substituted phenylazo, $Y^2$ is hydrogen, $Y^3$ is hydrogen or $C_1$–$C_4$-alkyl, $X^4$ is hydrogen, $C_1$–$C_4$-alkyl, $C_1$–$C_4$-dialkylamino or $C_1$–$C_{16}$-monoalkylamino, $X^5$ is hydrogen or $C_1$–$C_4$-alkyl, and $X^6$ is hydrogen, $C_1$–$C_4$-alkyl or $C_1$–$C_4$-alkoxy, with the proviso that a) at least one of the three radicals $Y^1$, $Y^2$ and $Y^3$ is different from hydrogen, b) $Y^2$ may also be cyano when $X^4$ is $C_1$–$C_4$-dialkylamino, c) $Y^2$ may also be $C_1$–$C_4$-alkoxycarbonyl when all the radicals $X^4$, $X^5$ and $X^6$ are different from hydrogen, and d) one of the radicals $Y^1$, $Y^2$ or $Y^3$ or may also be nitro when $X^4$ is $C_1$–$C_{16}$-monoalkylamino and $X^6$ is $C_1$–$C_4$-alkyl.

Preference is given to azo dyes of the formula II where $Y^1$ is hydrogen.

The novel azo dyes of the formula II are obtainable in a conventional manner, for example by diazotizing an aniline of the formula III

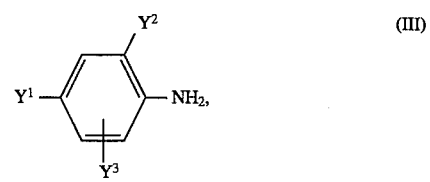

where $Y^1$, $Y^2$ and $Y^3$ are each as defined above, and coupling the resulting diazonium compound with a phenol of the formula IV

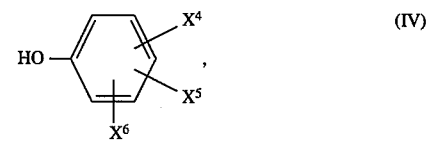

where $X^4$, $X^5$ and $X^6$ are each as defined above.

The further azo dyes of the formula I and those of the formula Ia are generally compounds known per se. They are described for example in U.S. Pat. No. 5,156,653 or U.S. Pat. No. 4,473,376 or can be obtained by the methods mentioned therein.

The Examples which follow illustrate the invention (parts are by weight).

EXAMPLE 1

Commercial diesel fuel was admixed with 10 ppm of a dye (F1) of the formula

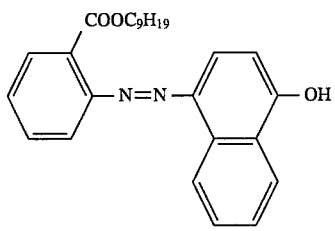
5

9 parts of the diesel fuel thus marked red were admixed with 0.5 part of a mixture of 4 parts of distilled water, 4 parts of 1,10-diamino-4,7-dioxadecane and 2 parts of 10% strength by weight sodium hydroxide solution and vigorously shaken. After about 1 min an aqueous phase with a strong red color separated off as bottom layer. The supernatant diesel fuel phase was almost colorless. The coloring of the aqueous phase was unchanged after 24 h at room temperature.

A blank test carried out on unmarked diesel oil under similar conditions produced an aqueous phase which was almost colorless.

Performing the reaction under similar conditions with a commercial gasoline (from Aral) marked with the dye F1 produced the same color effect as was obtained in the case of marked diesel fuel.

A blank test carried out on unmarked gasoline (from Aral) under similar conditions produced an aqueous phase which was almost colorless.

Similar detection results were achieved on diesel fuel marked with the dyes listed below using various reagent solutions likewise listed below.

Dyes:

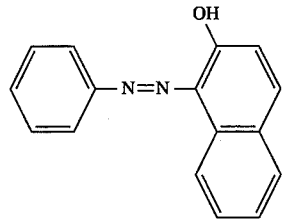
F2

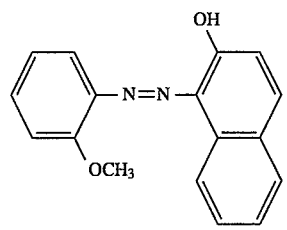
F3

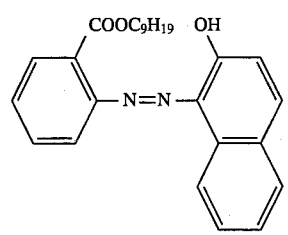
F4

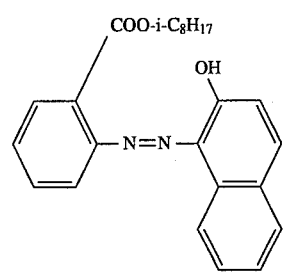
F-5

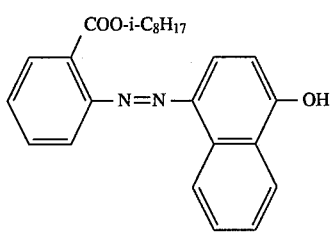
F6

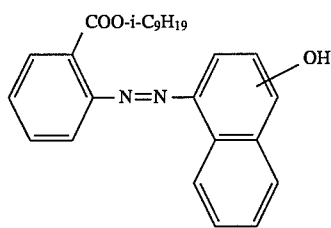
F7

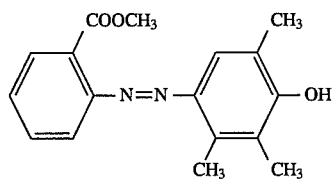
F8

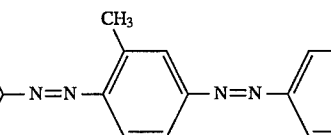
F9

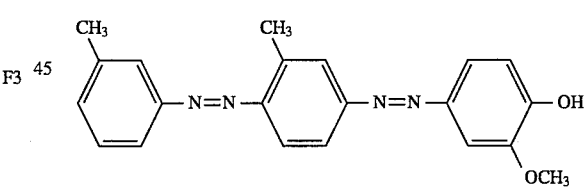
F10

F11

-continued

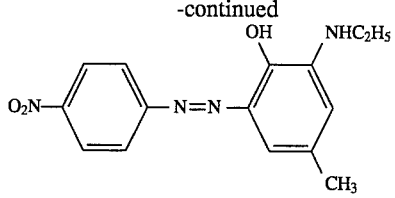

F12

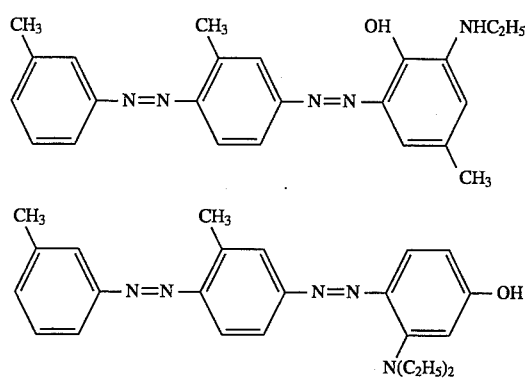

F13

F14

Reagent solutions:

R1  9 parts of NMP and 1 part of 1% strength by weight aqueous lithium hydroxide solution R2  9 parts of 2-pyrrolidinone and 1 part of 1% strength by weight aqueous lithium hydroxide solution R3  9 parts of DMSO and 1 part of 2% strength by weight aqueous lithium hydroxide solution R4  9.5 parts of 1-methylimidazole and 0.5 part of 5% strength by weight aqueous lithium hydroxide solution R5  9.5 parts of amine of formula $H_2N-CH(CH_3)CH_2[-OCH(CH_3)CH_2]_{2,6}-OCH_2CH(CH_3)-NH_2$ and 0.5 part of 1% strength by weight aqueous lithium hydroxide solution R6  9 parts of 1,3-dimethylhexahydropyrimid-2-one and 1 part of 1% strength by weight aqueous lithium hydroxide solution R7  9 parts of 1,13-diamino-4,7,10-trioxatridecane and 1 part of 1% strength by weight aqueous lithium hydroxide solution R8  5 parts of 3-methoxypropylamine and 1 part of 5% strength by weight aqueous potassium hydroxide solution R9  4 parts of distilled water, 4 parts of 1,10-diamino-4,7-dioxadecane and 2 parts of 10% strength by weight sodium hydroxide solution R10  9 parts of DMSO, 1 part of 2% strength by weight aqueous lithium hydroxide solution and 1 part of 4-nonylphenol The following results were obtained:

| Ex. No. | Dye | Reagent | Hue of aqueous phase | Hue of oily phase after shaking | Hue of oily phase before shaking | Marker concentration in diesel fuel |
|---|---|---|---|---|---|---|
| 2 | F1 | R1 | strongly red | colorless | strongly yellow | 10 ppm |
| 3 | F1 | R2 | strongly red | colorless | strongly yellow | 10 ppm |
| 4 | F1 | R3 | strongly red | colorless | strongly yellow | 10 ppm |
| 5 | F1 | R4 | strongly red | colorless | strongly yellow | 10 ppm |
| 6 | F1 | R8 | weakly red | weakly yellow | strongly yellow | 10 ppm |
| 7 | F1 | R10 | strongly red | almost colorless | strongly yellow | 10 ppm |
| 8 | F2 | R1 | strongly orange | colorless | strongly orange | 5 ppm |
| 9 | F2 | R2 | strongly orange | colorless | strongly orange | 5 ppm |
| 10 | F2 | R3 | strongly orange | almost colorless | strongly orange | 5 ppm |
| 11 | F2 | R4 | yellowish orange | weakly yellow | strongly orange | 5 ppm |
| 12 | F2 | R5 | strongly orange | colorless | strongly orange | 5 ppm |
| 13 | F2 | R6 | strongly orange | slightly yellow | strongly orange | 5 ppm |
| 14 | F2 | R7 | strongly orange | colorless | strongly orange | 5 ppm |
| 15 | F2 | R8 | strongly orange | almost colorless | strongly orange | 5 ppm |
| 16 | F2 | R9 | orange | slightly yellow | strongly orange | 5 ppm |
| 17 | F2 | R10 | strongly orange | almost colorless | strongly orange | 5 ppm |
| 18 | F3 | R1 | strongly orange | almost colorless | strongly orange | 5 ppm |
| 19 | F3 | R2 | strongly orange | colorless | strongly orange | 5 ppm |
| 20 | F3 | R3 | strongly orange | almost colorless | strongly orange | 5 ppm |
| 21 | F3 | R4 | strongly orange | weakly orange | strongly orange | 5 ppm |
| 22 | F3 | R5 | strongly orange | colorless | strongly orange | 5 ppm |
| 23 | F3 | R6 | strongly orange | almost colorless | strongly orange | 5 ppm |
| 24 | F3 | R7 | strongly orange | colorless | strongly orange | 5 ppm |
| 25 | F3 | R8 | orange | weakly orange | strongly orange | 5 ppm |
| 26 | F3 | R9 | strongly orange | weakly orange | strongly orange | 5 ppm |
| 27 | F3 | R10 | strongly orange | almost colorless | strongly orange | 5 ppm |
| 28 | F4 | R1 | strongly red | colorless | strongly yellow | 10 ppm |
| 29 | F4 | R2 | strongly red | colorless | strongly yellow | 10 ppm |
| 30 | F4 | R3 | strongly red | almost colorless | strongly yellow | 10 ppm |
| 31 | F4 | R8 | yellow | weakly yellow | strongly yellow | 10 ppm |
| 32 | F4 | R9 | weakly yellow | weakly yellow | strongly yellow | 10 ppm |
| 33 | F4 | R10 | strongly yellow | weakly yellow | strongly yellow | 10 ppm |
| 34 | F5 | R1 | strongly orange | slightly yellow | strongly yellow | 10 ppm |
| 35 | F5 | R2 | strongly orange | slightly yellow | strongly yellow | 10 ppm |
| 36 | F5 | R3 | strongly orange | almost colorless | strongly yellow | 10 ppm |
| 37 | F5 | R8 | yellow | weakly yellow | strongly yellow | 10 ppm |
| 38 | F5 | R9 | weakly yellow | weakly yellow | strongly yellow | 10 ppm |
| 39 | F5 | R10 | strongly orange | weakly orange | strongly yellow | 10 ppm |
| 40 | F6 | R1 | strongly orange | colorless | strongly yellow | 10 ppm |
| 41 | F6 | R2 | strongly orange | colorless | strongly yellow | 10 ppm |
| 42 | F6 | R3 | strongly | almost | strongly | 10 ppm |

| Ex. No. | Dye | Re-agent | Hue of aqueous phase | Hue of oily phase after shaking | Hue of oily phase before shaking | Marker concentration in diesel fuel |
|---|---|---|---|---|---|---|
| 43 | F6 | R8 | orange strongly red | colorless almost colorless | yellow strongly yellow | 10 ppm |
| 44 | F6 | R9 | strongly red | weakly yellow | strongly yellow | 10 ppm |
| 45 | F6 | R10 | strongly red | almost colorless | strongly yellow | 10 ppm |
| 46 | F7 | R1 | strongly red | slightly yellow | strongly yellow | 5 ppm |
| 47 | F7 | R2 | strongly red | almost colorless | strongly yellow | 5 ppm |
| 48 | F7 | R3 | strongly reddish violet | almost colorless | strongly yellow | 5 ppm |
| 49 | F7 | R8 | strongly red | almost colorless | strongly yellow | 5 ppm |
| 50 | F7 | R9 | strongly red | weakly yellow | strongly yellow | 5 ppm |
| 51 | F7 | R10 | strongly red | almost colorless | strongly yellow | 5 ppm |
| 52 | F8 | R1 | strongly orange | almost colorless | strongly yellow | 20 ppm |
| 53 | F8 | R2 | strongly orange | almost colorless | strongly yellow | 20 ppm |
| 54 | F8 | R3 | strongly orange | almost colorless | strongly yellow | 20 ppm |
| 55 | F8 | R8 | strongly orange | weakly yellow | strongly yellow | 20 ppm |
| 56 | F8 | R9 | weakly yellow | weakly yellow | strongly yellow | 20 ppm |
| 57 | F8 | R10 | strongly orange | slightly yellow | strongly yellow | 20 ppm |
| 58 | F9 | R1 | orange | weakly yellow | strongly yellow | 5 ppm |
| 59 | F9 | R2 | strongly orange | weakly orange | strongly yellow | 5 ppm |
| 60 | F9 | R3 | strongly orange | almost colorless | strongly yellow | 5 ppm |
| 61 | F9 | R4 | strongly red | almost colorless | strongly yellow | 5 ppm |
| 62 | F9 | R5 | strongly orange | weakly orange | strongly yellow | 5 ppm |
| 63 | F9 | R6 | strongly orange | weakly orange | strongly yellow | 5 ppm |
| 64 | F9 | R7 | strongly orange | weakly orange | strongly yellow | 5 ppm |
| 65 | F9 | R8 | orange | weakly orange | strongly yellow | 5 ppm |
| 66 | F9 | R9 | strongly bright red | weakly yellow | strongly yellow | 10 ppm |
| 67 | F9 | R10 | strongly red | weakly yellow | strongly yellow | 10 ppm |
| 68 | F10 | R1 | strongly violet | almost colorless | strongly yellow | 5 ppm |
| 69 | F10 | R2 | strongly violet | almost colorless | strongly yellow | 5 ppm |
| 70 | F10 | R3 | strongly dark blue | almost colorless | strongly yellow | 5 ppm |
| 71 | F10 | R4 | strongly green | weakly green | strongly yellow | 5 ppm |
| 72 | F10 | R5 | strongly violet | weakly red | strongly yellow | 5 ppm |
| 73 | F10 | R6 | strongly violet | almost colorless | strongly yellow | 5 ppm |
| 74 | F10 | R7 | strongly bluish gray | almost colorless | strongly yellow | 5 ppm |
| 75 | F10 | R8 | strongly reddish violet | almost colorless | strongly yellow | 5 ppm |
| 76 | F10 | R9 | strongly red | weakly yellow | strongly yellow | 5 ppm |
| 77 | F10 | R10 | strongly | almost | strongly | |
| 78 | F11 | R1 | strongly violet | almost colorless | strongly yellow | 5 ppm |
| 79 | F11 | R2 | strongly yellowish orange | weakly yellow | strongly yellow | 5 ppm |
| 80 | F11 | R3 | strongly violet | almost colorless | strongly yellow | 5 ppm |
| 81 | F11 | R4 | strongly orange | weakly yellow | strongly yellow | 5 ppm |
| 82 | F11 | R5 | strongly orange | weakly yellow | strongly yellow | 5 ppm |
| 83 | F11 | R6 | strongly orange | weakly yellow | strongly yellow | 5 ppm |
| 84 | F11 | R7 | strongly orange | weakly yellow | strongly yellow | 5 ppm |
| 85 | F11 | R8 | strongly orange | weakly yellow | strongly yellow | 5 ppm |
| 86 | F11 | R9 | strongly red | weakly yellow | strongly yellow | 5 ppm |
| 87 | F11 | R10 | strongly dark red | weakly yellow | strongly yellow | 5 ppm |
| 88 | F12 | R1 | strongly reddish violet | almost colorless | strongly yellow | 5 ppm |
| 89 | F12 | R2 | strongly violet | almost colorless | strongly yellow | 5 ppm |
| 90 | F12 | R3 | strongly violet | almost colorless | strongly yellow | 5 ppm |
| 91 | F12 | R4 | strongly green | almost colorless | strongly yellow | 5 ppm |
| 92 | F12 | R5 | strongly reddish violet | almost colorless | strongly yellow | 5 ppm |
| 93 | F12 | R6 | strongly dark blue | almost colorless | strongly yellow | 5 ppm |
| 94 | F12 | R7 | strongly reddish violet | almost colorless | strongly yellow | 5 ppm |
| 95 | F12 | R8 | strongly bright blue | almost colorless | strongly yellow | 5 ppm |
| 96 | F12 | R9 | strongly bright blue | weakly yellow | strongly yellow | 5 ppm |
| 97 | F12 | R10 | strongly violet | weakly yellow | strongly yellow | 5 ppm |
| 98 | F13 | R1 | strongly yellowish brown | weakly yellow | strongly orange | 5 ppm |
| 99 | F13 | R2 | strongly reddish brown | weakly yellow | strongly orange | 5 ppm |
| 100 | F13 | R3 | strongly reddish violet | weakly yellow | strongly orange | 5 ppm |
| 101 | F13 | R4 | strongly yellow | weakly yellow | strongly orange | 5 ppm |
| 102 | F13 | R5 | strongly red | weakly yellow | strongly orange | 5 ppm |
| 103 | F13 | R6 | strongly yellowish green | weakly yellow | strongly orange | 5 ppm |
| 104 | F13 | R7 | yellowish brown | weakly yellow | strongly orange | 5 ppm |
| 105 | F13 | R8 | greenish gray | weakly yellow | strongly orange | 5 ppm |
| 106 | F13 | R9 | colorless | weakly yellowish orange | strongly orange | 5 ppm |
| 107 | F13 | R10 | strongly reddish brown | weakly yellow | strongly orange | 5 ppm |
| 108 | F14 | R1 | strongly | weakly | strongly | 5 ppm |

-continued

| Ex. No. | Dye | Re- agent | Hue of aqueous phase | Hue of oily phase after shaking | Hue of oily phase before shaking | Marker concen- tration in diesel fuel |
| --- | --- | --- | --- | --- | --- | --- |
| 109 | F14 | R2 | orange strongly orange | yellow weakly yellow | yellow strongly yellow | 5 ppm |
| 110 | F14 | R3 | strongly orange | weakly yellow | strongly yellow | 5 ppm |
| 111 | F14 | R4 | strongly yellow | weakly yellow | strongly yellow | 5 ppm |
| 112 | F14 | R5 | strongly orange | weakly yellow | strongly yellow | 5 ppm |
| 113 | F14 | R6 | strongly orange | weakly yellow | strongly yellow | 5 ppm |
| 114 | F14 | R7 | strongly orange | weakly yellow | strongly yellow | 5 ppm |
| 115 | F14 | R8 | strongly orange | weakly yellow | strongly yellow | 5 ppm |
| 116 | F14 | R9 | strongly orange | weakly yellow | strongly yellow | 5 ppm |
| 117 | F14 | R10 | strongly orange | weakly yellow | strongly yellow | 5 ppm |

EXAMPLE 118 (Preparation of F7)

a) 42.6 g (0.04 mol) of m-aminoazotoluene hydrochloride (24.5% strength by weight) and 0.2 g of a wetting agent were suspended in 32 ml of water and 12 ml of 30% strength by weight hydrochloric acid. The suspension was then admixed with 20 g of ice, 7 ml of toluene and 12 ml of 23% strength by weight aqueous sodium nitrite solution and stirred at from 5 to 10° C. for 2 h.

b) 3..76 g (0.04 mol) of phenol and 100 ml of water were adjusted with 50% strength by weight sodium hydroxide solution to pH 6.4 and admixed at 0° C. with the diazonium salt solution described under a). The pH was held between 4 and 5 with 10% strength by weight sodium hydroxide solution. After stirring overnight the pH was reduced to 1.5 with 10% strength by weight hydrochloric acid and the precipitated solid was isolated.

Yield: 10.1 g

EXAMPLE 119 (Preparation of F9)

a) 3.0 g (0.02 mol) of methyl anthranilate were dissolved at 0° C. in 30 ml of water, 50 g of ice and 5 ml of concentrated hydrochloric acid and then admixed with 6 ml of 23% strength by weight aqueous sodium nitrite solution. The mixture was then stirred at from 0° to 5° C. for 30 minutes until a clear solution had formed.

b) 2.7 g (0.02 mol) of 2,3,6-trimethylphenol in 100 ml of water were adjusted with 50% strength by weight sodium hydroxide solution to pH 13 and admixed with the diazonium salt solution described under a). After stirring overnight the pH was reduced to 2.1 with 10% strength by weight hydrochloric acid and the precipitated solid was isolated.

Yield: 5.8 g

EXAMPLE 120 (Preparation of F12)

a) 7.19 g (0.05 mol) of p-nitroaniline and 0.1 g of a wetting agent were suspended in 45 ml of water and 17.5 ml of 30% strength by weight hydrochloric acid. The suspension was then admixed with 55 g of ice and 16.5 ml of 23% strength by weight aqueous sodium nitrite solution and stirred at from 0° to 5° C. for 1 h.

b) 7.56 g (0.05 mol) of 2-monoethylamino-4-methylphenol were added to 100 ml of water and adjusted with 50% strength by weight sodium hydroxide solution to pH 10. Then the diazonium salt solution described under a) was added at 5° C. The pH was held between 7 and 8 with 10% strength by weight sodium hydroxide solution. After stirring overnight the pH dropped to 4.6 and the precipitated solid was filtered off with suction.

Yield: 14.1 g

EXAMPLE 121 (Preparation of F13)

a) 53.3 g (0.05 mol) of m-aminoazotoluene hydrochloride (24.5% strength by weight) and 0.2 g of a wetting agent were suspended in 40 ml of water and 15 ml of 30% strength by weight hydrochloric acid. The suspension was then admixed with 25 g of ice, 8.4 ml of toluene and 15 ml of 23% strength by weight aqueous sodium nitrite solution and stirred at from 5 to 10° C. for 2 h.

b) 7.56 g (0.05 mol) of 2-monoethylamino-4-methylphenol were added to 100 ml of water and pH 10 was set with 50% strength by weight sodium hydroxide solution. Then the diazonium salt solution described under a) was added at 5° C. The pH was held between 7 and 8 with 10% strength by weight sodium hydroxide solution. After stirring overnight the pH was adjusted with hydrochloric acid to 1.5 and the precipitated solid was filtered off with suction.

Yield: 15.9 g

EXAMPLE 122 (Preparation of F14)

a) 42.6 g (0.04 mol) of m-aminoazotoluene hydrochloride (24.5% strength by weight) and 0.2 g of a wetting agent were suspended in 32 ml of water and 12 ml of 30% strength by weight hydrochloric acid. The suspension was then admixed with 20 g of ice, 7 ml of toluene and 12 ml of 23% strength by weight aqueous sodium nitrite solution and stirred at from 5 to 10° C. for 2 h.

b) 6.7 g (0.04 mol) of m-N,N-diethylaminophenol were added to 100 ml of water and pH 13.2 was set with 50% strength by weight sodium hydroxide solution. Then the diazonium salt solution described under a) was added at 5° C. The pH was held between 4 and 5 with 10% strength by weight sodium hydroxide solution. After stirring overnight the pH was reduced to 1.5 with 10% strength by weight hydrochloric acid and the precipitated solid was isolated.

Yield: 16 g

The same method gives the dyes F10 and F11.

We claim:

1. A method for detecting azo dye marked mineral oils by treating the marked mineral oil with an extractant comprising water, a solvent and a base, the azo dye transferring from the mineral oil into the aqueous phase, which comprises using as marker an azo dye of the formula I $$X^1 \!-\!\!\begin{array}{c} X^2 \\ | \\ \bigcirc \\ | \\ X^3 \end{array}\!\!-\! N\!=\!N \!-\!\begin{array}{c} \\ \bigcirc A \\ (X^4)_m \end{array}\!\!-\! OH \qquad (I)$$

where ring A may be benzofused, m is from 1 to 4, $X^1$ is hydrogen, $C_1$–$C_4$-alkyl, cyano or nitro, $X^2$ is hydrogen, $C_1$–$C_4$-alkyl, cyano, nitro, $C_1$–$C_4$-alkoxy or $C_1$–$C_{16}$-alkoxycarbonyl, $X^3$ is hydrogen, $C_1$–$C_4$-alkyl, cyano or $C_1$–$C_{16}$-alkoxycarbonyl, and $X^4$ is hydrogen, hydroxyl, $C_1$–$C_8$-alkyl, which may be phenyl-substituted, $C_1$–$C_4$-alkoxy, amino, $C_1$–$C_4$-dialkylamino or $C_1$–$C_{16}$-monoalkylamino whose alkyl chain may be interrupted by from 1 to 3 oxygen atoms in the ether function, as solvent a partially or completely water-miscible organic solvent, and as base an alkali or alkaline earth metal hydroxide, an alkali metal carbonate or an ammonium compound of the formula

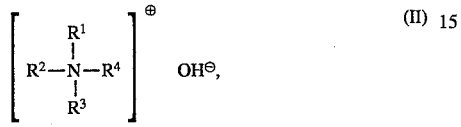

where $R^1$, $R^2$, $R^3$ and $R^4$ are each independently of the others $C_1$–$C_{16}$-alkyl or benzyl.

2. A method as claimed in claim 1, wherein the azo dye used has the formula Ia

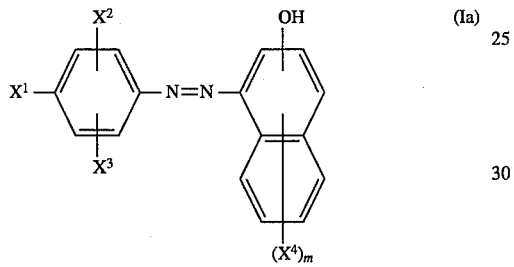

where m is from 1 to 4, $X^1$ is hydrogen, cyano or nitro, $X^2$ is hydrogen, $C_1$–$C_4$-alkyl, $C_1$–$C_4$-alkoxy or $C_1$–$C_{13}$-alkoxycarbonyl, $X^3$ is hydrogen or $C_1$–$C_4$-alkyl, and $X^4$ is hydrogen or $C_1$–$C_8$-alkyl, which may be phenyl-substituted.

3. A method as claimed in claim 1, wherein the azo dye used has the formula Ib

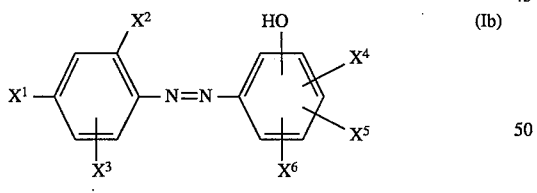

where $X^1$ is hydrogen, $X^2$ is hydrogen, $X^3$ is hydrogen or $C_1$–$C_4$-alkyl, $X^4$ is hydrogen, $C_1$–$C_4$-alkyl, $C_1$–$C_4$-dialkylamino or $C_1$–$C_{16}$-monoalkylamino, $X^5$ is hydrogen or $C_1$–$C_4$-alkyl, and $X^6$ is hydrogen, $C_1$–$C_4$-alkyl or $C_1$–$C_4$-alkoxy, with the proviso that a) at least one of the three radicals $X^1$, $X^2$ and $X^3$ is different from hydrogen, b) $X^2$ may also be cyano when $X^4$ is $C_1$–$C_4$-dialkylamino, c) $X^2$ may also be $C_1$–$C_4$-alkoxycarbonyl when all the radicals $X^4$, $X^5$ and $X^6$ are different from hydrogen, and d) one of the radicals $X^1$, $X^2$ or $X^3$ may also be nitro when $X^4$ is $C_1$–$C_{16}$-monoalkylamino and $X^6$ is $C_1$–$C_4$-alkyl.

4. A method as claimed in claim 1, wherein the base used is an alkali or alkaline earth metal hydroxide.

5. A method of marking a mineral oil, comprising adding to said mineral oil an effective amount therefor consisting of an azo dye of the formula Ia

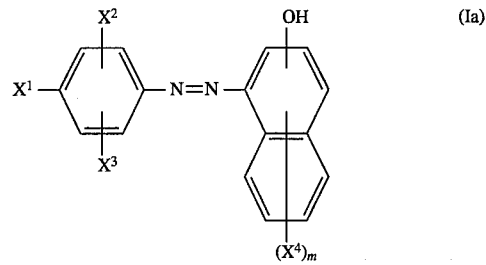

where m is from 1 to 4, $X^1$ is hydrogen, cyano or nitro, $X^2$ is hydrogen, $C_1$–$C_4$-alkyl, $C_1$–$C_4$-alkoxy or $C_1$–$C_{13}$-alkoxycarbonyl, $X^3$ is hydrogen or $C_1$–$C_4$-alkyl, and $X^4$ is hydrogen or $C_1$–$C_4$-alkyl, which may be phenyl-substituted.

6. A method as claimed in claim 5 where $X^4$ is hydrogen or 1-phenylethyl.

7. A method as claimed in claim 5 where $X^1$ is hydrogen, $X^2$ is methyl or $C_1$–$C_{13}$-alkoxycarbonyl, and $X^3$ is hydrogen or methyl.

8. A method as claimed in claim 5 of azo dyes conforming to the formula Ic

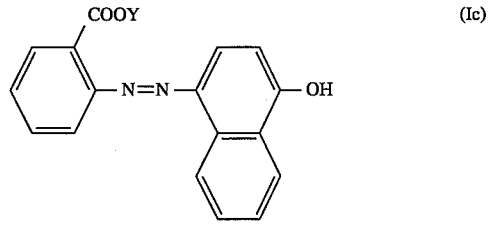

where

Y is $C_7$–$C_{11}$-alkyl.

9. A method of marking a mineral oil, comprising adding to said mineral oil an effective amount therefor of an azo dye of the formula Ib

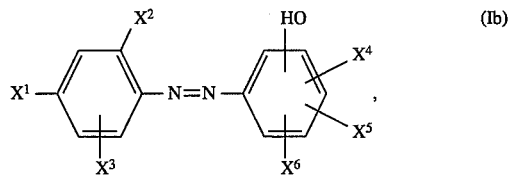

where $X^1$ is hydrogen, $X^2$ is hydrogen, $X^3$ is hydrogen or $C_1$–$C_4$-alkyl, $X^4$ is hydrogen, $C_1$–$C_4$-alkyl, $C_1$–$C_4$-dialkylamino or $C_1$–$C_{16}$-monoalkylamino, $X^5$ is hydrogen or $C_1$–$C_4$-alkyl, and $X^6$ is hydrogen, $C_1$–$C_4$-alkyl or $C_1$–$C_4$-alkoxy, with the proviso that a) at least one of the three radicals $X^1$, $X^2$ and $X^3$ is different from hydrogen, b) $X^2$ may also be cyano when $X^4$ is $C_1$–$C_4$-dialkylamino, c) $X^2$ may also be $C_1$–$C_4$-alkoxycarbonyl when all the radicals $X^4$, $X^5$ and $X^6$ are different from hydrogen, and d) one of the radicals $X^1$, $X^2$ or $X^3$ may also be nitro when $X^4$ is $C_1$–$C_{16}$-monoalkylamino and $X^6$ is $C_1$–$C_4$-alkyl.

10. Azo dyes of the formula II

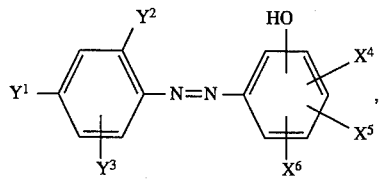

where $Y^1$ is hydrogen, or $C_1$–$C_4$-alkyl-substituted phenylazo, $Y^2$ is hydrogen, $Y^3$ is hydrogen or $C_1$–$C_4$-alkyl, $X^4$ is hydrogen, $C_1$–$C_4$-alkyl, $C_1$–$C_4$-dialkylamino or $C_{11}$–$C_{16}$-monoalkylamino, $X^5$ is hydrogen or $C_1$–$C_4$-alkyl, and $X^6$ is hydrogen, $C^1$–$C_4$-alkyl or $C_1$–$C_4$-alkoxy, with the proviso that a) at least one of the three radicals $Y^1$, $Y^2$ and $Y^3$ is different from hydrogen, b) $Y^2$ may also be cyano when $X^4$ is $C_1$–$C_4$-dialkylamino, c) $Y^2$ may also be $C_1$–$C_4$-alkoxycarbonyl when all the radicals $X^4$, $X^5$ and $X^6$ are different from hydrogen, and d) one of the radicals $Y^1$, $Y^2$ or $Y^3$ may also be nitro when $X^4$ is $C_1$–$C_{16}$-monoalkylamino and $X^6$ is $C_1$–$C_4$-alkyl.

* * * * *